US00PP27950P3

(12) United States Plant Patent
Randag

(10) Patent No.: US PP27,950 P3
(45) Date of Patent: Apr. 25, 2017

(54) CALLA LILY PLANT NAMED 'SIBERIA'

(50) Latin Name: *Zantedeschia sprengeri*
Varietal Denomination: Siberia

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 85 days.

(21) Appl. No.: 14/544,477

(22) Filed: Jan. 12, 2015

(65) Prior Publication Data

US 2015/0296693 P1 Oct. 15, 2015

Related U.S. Application Data

(60) Provisional application No. 61/964,771, filed on Apr. 11, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV—International Union for the Protection of New Varieties of Plants: PLUTO Plant Variety Database; Jun. 11, 2016; cultivar name—'Siberia' (1 pg).*

* cited by examiner

*Primary Examiner* — Susan McCormick Ewoldt
(74) *Attorney, Agent, or Firm* — The Webb Law Firm

(57) ABSTRACT

'Siberia' is a new variety of calla lily having inflorescences with a white-colored spathe that produces 4-18 inflorescences per tuber. The inflorescence stems are about 60 cm in height, and the leaves are green with whitish spots and have a leathery texture.

3 Drawing Sheets

Botanical classification: *Zantedeschia sprengeri*.
Varietal denomination: 'SIBERIA'.

BACKGROUND OF THE NEW PLANT

The present invention comprises a new and distinct cultivar of calla lily, botanically known as *Zantedeschia sprengeri* and hereinafter referred to by the cultivar name 'Siberia'.

'Siberia' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* 'Z010448' with a *Zantedeschia sprengeri* variety Chrystal Blush (male parent, unpatented). 'Siberia' was selected in 2006 by the inventor in 't Zand, The Netherlands as one flowering plant within the progeny of the stated cross.

The first act of asexual reproduction of 'Siberia' by tissue culture was performed by the inventor in September of 2008 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Siberia' which, in combination, distinguish this calla lily as a new and distinct cultivar:

1. White-colored spathe;
2. White linear spots in leaves; and
3. High inflorescence production.

Further, when compared to calla lily plant named 'Sapporo' (unpatented), the upper and lower surface spathe color of 'Sapporo' is White Group RHS 155C, while the upper surface spathe color of 'Siberia' varies between White Group RHS 155B and Green-White Group RHS 157C and the lower surface spathe color of 'Siberia' varies between Yellow-Green Group RHS 150B and 150C. Further, 'Sapporo' has from 3-6 branches, while 'Siberia' has from 3-10 branches. Additionally, 'Siberia' exhibits more numerous leaf maculation spots than 'Sapporo'.

Table 1 provides similarities and differences of 'Siberia' to its parents, *Zantedeschia sprengeri* 'Z010448' and variety Chrystal Blush.

TABLE 1

| 'Siberia' | Similarities | Differences |
|---|---|---|
| Z010448 | Spathe size<br>Plant height | Spathe color (Varies between Yellow-White Group RHS 158A and 158C) |
| Chrystal Blush | Leaf shape<br>Plant height | Number of inflorescences (5-15)<br>Smaller spathe size<br>No spots on leaves |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

THE PLANT

Figure 1:
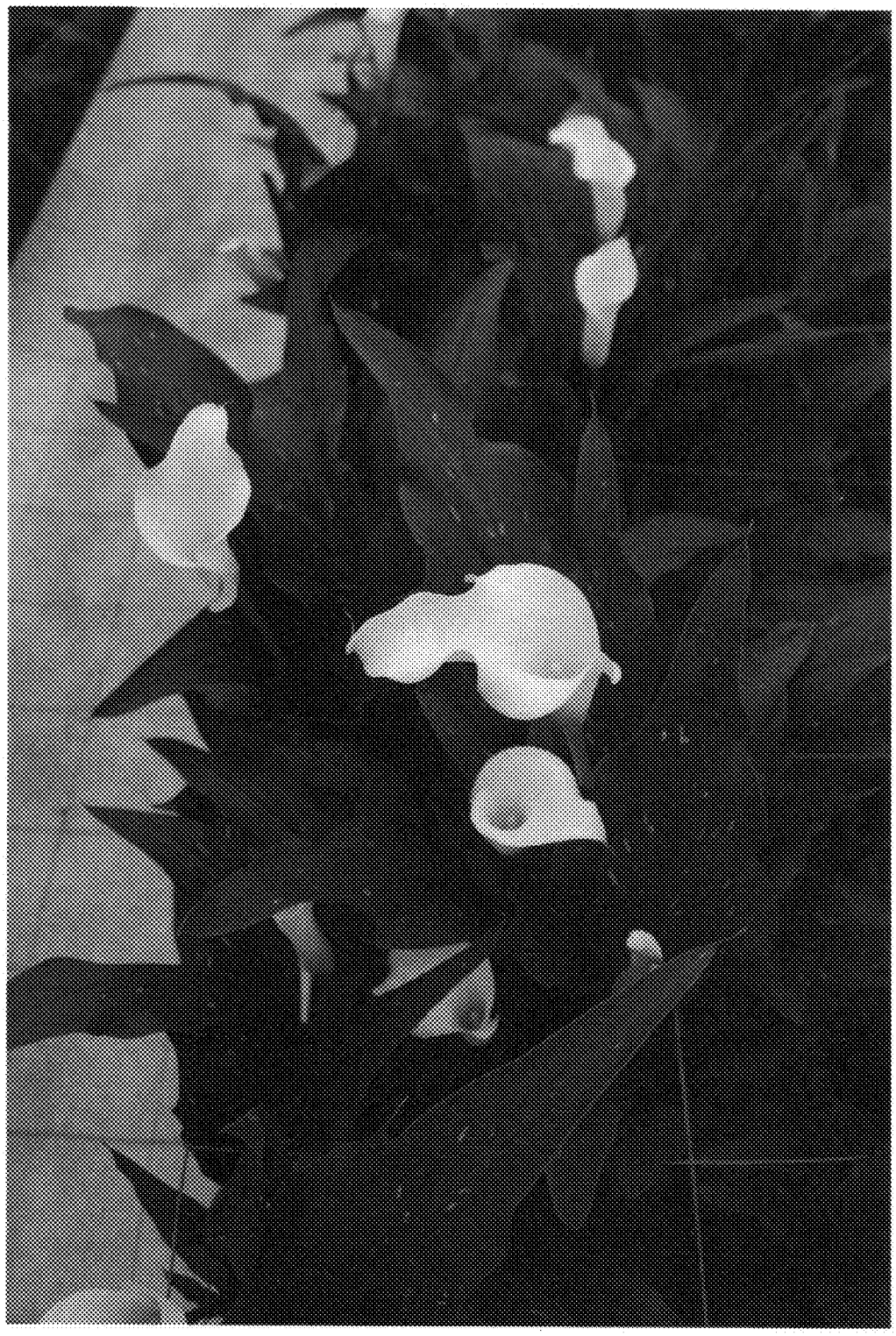
FIG. 1 Single Siberia plant
Figure 2:
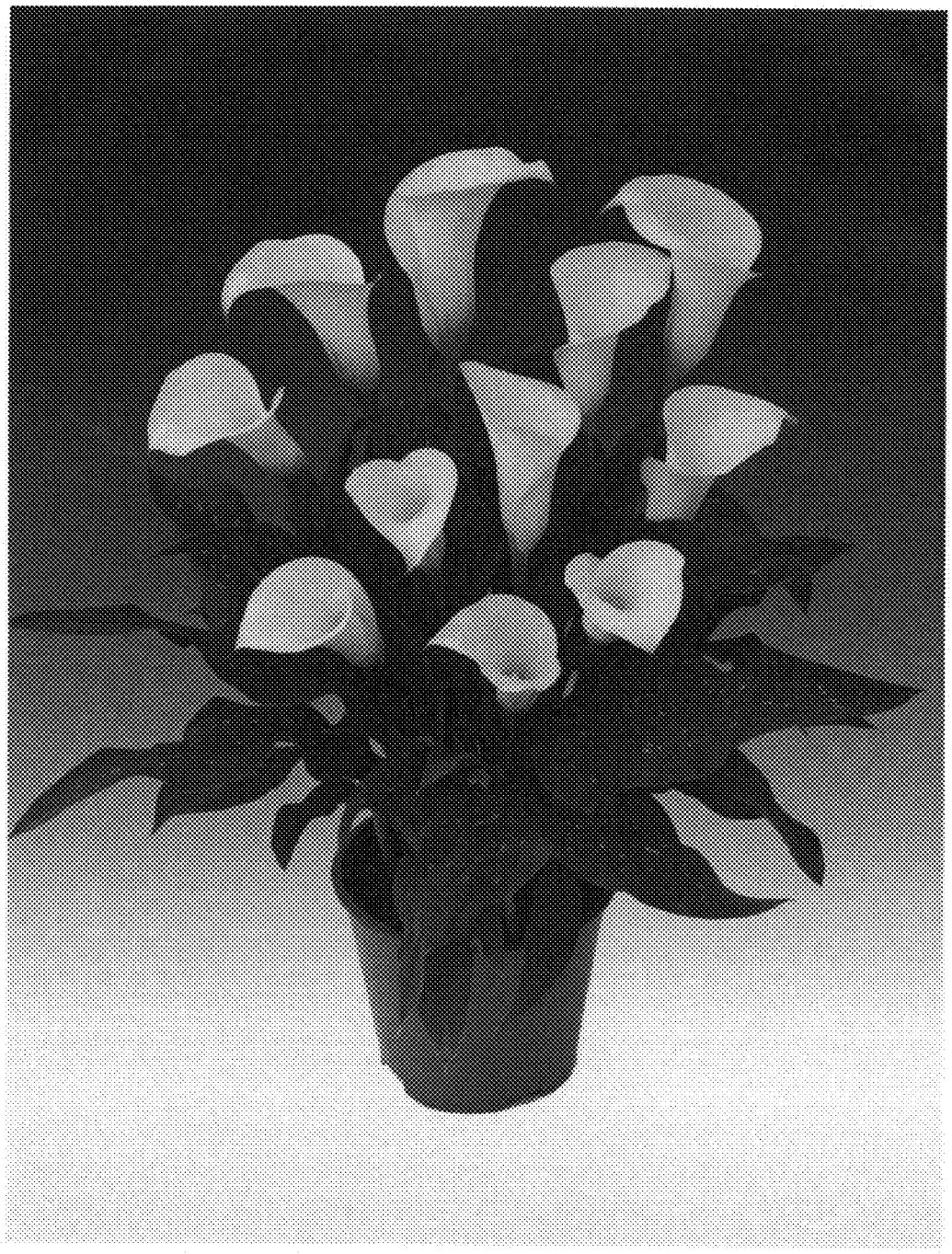
FIG. 2. Potted Siberia plant
Figure 3:
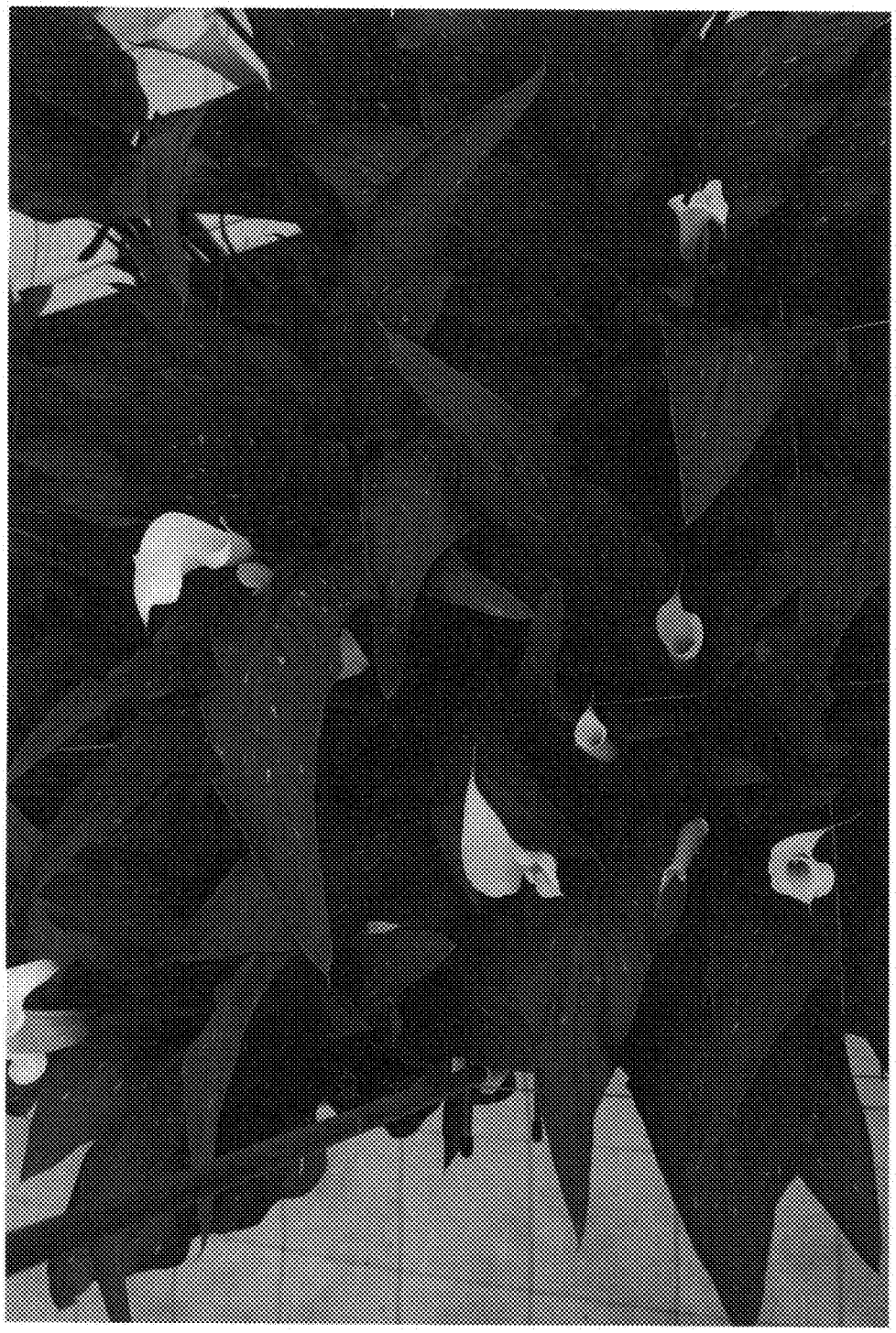
FIG. 3. Group of Siberia plants

Size:

*Height of the leaf canopy above the soil.*—20-70 cm.

*Height of top of inflorescence above the soil.*—30-80 cm.

*Diameter.*—20-55 cm.

Form: Erect.

Number of inflorescences per tuber:

*Size* 14-16 cm *in diameter.*—4-8 inflorescences.

*Size* 16-18 cm *in diameter.*—7-10 inflorescences.

*Size* 18-20 cm *in diameter.*—8-18 inflorescences.

Branches:

*Character.*—Many (from 3-10); like the variety 'Odessa' (U.S. Plant Pat. No. 18,833).

*Color.*—Between RHS 144 B and 144 C.

Leaves:

*Size.*—Width: 2-15 cm. Length: 10-35 cm.

*Number per plant.*—20-50.

*Shape.*—Lanceolate.

*Color.*—Upper surface: RHS 139 A to 139 B, with transparent White Group RHS 155A and N155A spots. Lower surface: RHS 143A to 143B, with transparent White Group RHS 155A and N155A spots.

*Apex.*—Acute.

*Base.*—Round.

*Margin.*—Undulate; having a color of RHS 139 A to 139 B.

*Veins.*—Configuration: Pinnate. Color: RHS 144 B to 144 C.

*Surface quality.*—Leathery.

*Petiole.*—Length: 15-50 cm. Diameter: 15 mm. Color: The base is White Group RHS 155A, and the upper part is RHS 144 B to 144 C.

Roots:

*Color.*—White.

*Branching.*—Similar to other *Zantedeschia* varieties.

THE INFLORESCENCE AND SEEDS

Spathe:

*Size.*—Length (measured from opening to tip): 4.5-12 cm. Width: 4-7 cm. Height: 4-9 cm.

*Color.*—Upper surface: Varies between RHS 155 B and 157 C. Lower surface: Varies between RHS 150 B and 150 C.

Vein color.—Between RHS 155 B and 157 C.

*Shape.*—Cupped.

*Apex.*—Acute.

*Base.*—Attenuate.

*Texture.*—Smooth (upper and lower surfaces).

Spadix:

*Size.*—Length: 22-45 mm. Diameter: 3-7 mm.

*Color.*—Between RHS 9 B and 9 C.

*Position relative to spathe.*—Upright.

Peduncle:

*Size.*—Length: 25-65 cm. Diameter: 4-8 mm.

*Color.*—The upper part is between RHS 143 B and 143 C, and the lower part is Green-White Group RHS 157 C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Yellow Group RHS 9 B and 9 C.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between RHS 14 A and 14 B.

*Ovaries.*—Texture: Smooth. Length: Between 1 to 10 mm. Width: Between 1 to 10 mm. Color: Top color is between RHS 154 C and 154 D, bottom color is from White Group RHS 155B to 157C.

Seeds:

*Length.*—4-7 mm.

*Width.*—3-6 mm.

*Color.*—Between Yellow-Green Group RHS 150A and 151A.

*Amount.*—Between 1-50.

Fruit:

*Amount.*—Multiple berries produced.

*Shape.*—Irregular.

*Color.*—Varies between Yellow-Green Group RHS N144C and 145A.

GENERAL

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier — up to five weeks after planting Lastingness: About two weeks on the plant.

Fragrance: None.

I claim:

1. A new and distinct variety of calla lily plant named 'Siberia' as herein described and illustrated.

* * * * *